United States Patent [19]

Vorhauer et al.

[11] 4,393,871

[45] Jul. 19, 1983

[54] VAGINAL DEVICE

[75] Inventors: Bruce W. Vorhauer, Irvine; Thomas A. Dobbie, Jr., Newport Beach, both of Calif.

[73] Assignee: VLI Corporation, Costa Mesa, Calif.

[21] Appl. No.: 249,228

[22] Filed: Mar. 30, 1981

Related U.S. Application Data

[63] Continuation-in-part of Ser. No. 167,386, Jul. 9, 1980, abandoned, Ser. No. 96,295, Nov. 21, 1979, Ser. No. 96,293, Nov. 11, 1979, abandoned, Ser. No. 900,864, Apr. 28, 1978, which is a continuation-in-part of Ser. No. 810,109, Jun. 27, 1977, abandoned.

[51] Int. Cl.³ .............................. A61F 13/20
[52] U.S. Cl. ........................... 609/58; 128/127
[58] Field of Search .............. 128/260, 261, 263, 270, 128/285, 127, 130

[56] References Cited

U.S. PATENT DOCUMENTS

| 1,480,680 | 1/1924 | Glover. | |
|---|---|---|---|
| 2,020,107 | 11/1935 | Cruichshank. | |
| 3,128,762 | 4/1964 | Young. | |
| 3,916,898 | 11/1975 | Robinson | 128/270 |
| 3,918,452 | 11/1975 | Cornfeld. | |
| 3,978,855 | 9/1976 | McRae et al.. | |
| 3,993,073 | 11/1976 | Zaffaroni | 128/270 |
| 4,186,742 | 2/1980 | Donald | 128/270 |
| 4,193,813 | 3/1980 | Chvapil. | |
| 4,198,965 | 4/1980 | Strickman et al. | 128/127 |
| 4,228,797 | 10/1980 | Dickey | 128/270 |
| 4,274,410 | 6/1981 | Chvapil | 128/270 |

FOREIGN PATENT DOCUMENTS

| 1609913 | 6/1950 | Fed. Rep. of Germany. | |
|---|---|---|---|
| 822877 | 11/1951 | Fed. Rep. of Germany. | |
| 6933451 | 1/1970 | Fed. Rep. of Germany. | |
| 1189918 | 4/1904 | France. | |
| 7442623 | 12/1974 | France. | |
| WO79/0014 | 1/1979 | PCT Int'l Appl. | 128/270 |

Primary Examiner—C. Fred Rosenbaum

[57] ABSTRACT

A vaginal device adapted for insertion and placement in the human vaginal cavity and subsequent removal therefrom for the administration of spermicide or a variety of medications such as anti-infectives, anti-inflammatories, estrogens, progestogens, and the like. When used as a contraceptive, the vaginal device covers/blocks the cervix, soaks up and traps sperm, and slowly releases a spermicide.

24 Claims, 5 Drawing Figures

VAGINAL DEVICE

CROSS-REFERENCE TO RELATED APPLICATIONS

The present application is a continuation-in-part of copending applications Ser. No. 96,295, filed Nov. 21, 1979; Ser. No. 96,293, filed Nov. 11, 1979, now abandoned; Ser. No. 167,386, filed July 9, 1980, now abandoned; Ser. No. 900,864, filed Apr. 28, 1978, which is in turn a continuation-in-part of Ser. No. 810,109, filed June 27, 1977, and now abandoned. All of the aforementioned applications are incorporated herein by reference.

BACKGROUND OF THE INVENTION

The present invention relates to a removable vaginal device which can be used to administer medication or a spermicide.

One of the principal requirements for applying special medication to the body is that the medication remain in the desired body area for an extended period of time. For example, in the treatment of vaginal disorders, it is desirable that the medication be applied for many hours to remote regions of the vaginal canal and cervix. These regions are not readily reached by conventional vaginal suppositories due to their size and shape. Because of the structure and nature of the human vagina, inserted suppositories or ovules often do not stay in place, or, upon melting, the medication may drain out of the vagina, substantially reducing its effectiveness. In either of these cases, the medication is not maintained in the desired location for a sufficient duration of time, nor does it necessarily find its way to affected parts of the vaginal canal which are remote from the normal position of suppositories.

Prior attempts at overcoming these problems have not been satisfactory. For example, presently available medicated tampons do not extend far enough into the vaginal canal to deliver medication throughout the vaginal canal. Other medications are uncomfortable to insert and use because of their rigid structures.

Various attempts have been made to solve this problem of adequate delivery of medication to the vaginal canal, but the prior devices have been so far inadequate.

Groves, U.S. Pat. No. 3,815,600, teaches a vaginal medication to be retained within the human vaginal canal to apply medication molded thereon to the vaginal canal and cervix including a body-undissolvable stem and anchor means. However, for this device to be effective, it must be made rigid, and the rigidity can cause discomfort to many users.

Higuchi et al, U.S. Pat. No. 3,832,252, discloses a drug-delivery device for releasing medication at a controlled rate formed from a solid inner matrix containing medication dispersed therethrough surrounded by an outer membrane through which the medication diffuses. This device provides for a very slow release of medication.

Robinson, in U.S. Pat. No. 3,916,898, discloses a method for controlling estrus and ovulation in domestic animals by introducing into the vagina, and later removing, a sponge impregnated with a progestational compound. This device, however, is designed merely to increase fertility in domestic animals.

Roseman, U.S. Pat. No. 3,920,805, teaches a device for placement within a living body comprising a ring formed of a compatible polymeric material having medication in an outer coating of polymeric material which encircles a core of non-medicated polymeric material. This rigid ring may cause discomfort to the wearer.

Zaffaroni, U.S. Pat. No. 3,921,636, teaches a drug delivery device comprising a dry-permeable matrix comprising a plurality of drug reservoirs, each of which reservoirs comprises a drug surrounded by drug release rate controlling materials. This device relies on a drug release controlling material for efficacy, which release controlling material is of different structure and composition than the matrix material.

Laughlin et al, U.S. Pat. Nos. 4,031,202, and 4,067,961, discloses controlled release dosage devices for immediate delivery of any desired medicament. These devices comprise a stable, insoluble container, at least part of the wall of the container comprising a microporous membrane. The solid container may be uncomfortable to the user while it is in position in the vagina.

Roseman, U.S. Pat. No. 4,043,339, discloses devices for placement in the female human vaginal cavity for administering an abortifacient to the epithelial tissues of the vaginal cavity to produce abortion or to induce labor. A flexible, resilient, non-toxic polysiloxane elastomer is impregnated with an appropriate prostagladin.

Schopflin, U.S. Pat. No. 4,012,497, discloses a sustained release pharmaceutical composition containing one or more nonionic lypophilic drugs in a cured low temperature vulcanizable silicone elastomer excipient. The elastomer is cured in the presence of the drug.

Turning now to current contraceptive techniques, recently increasing attention has been given to the adverse reactions caused by oral contraceptives and intrauterine devices (IUD's), the two methods that are used by about 80% of the contracepting women in this country. Both the scientific and the lay presses have reported the occurrence of serious adverse side effects associated with their use, including myocardial infarction, thromboembolic disease, liver adenomas, pelvic inflammatory disease, ectopic pregnancy, and impaired fertility after discontinuing use of these methods.

Concurrent with the increased awareness of serious complications associated with the use of oral contraceptives and IUD's, there has been an increase in the number of users of barrier contraceptive methods. Research efforts have focused on the development of improved barrier contraceptive methods with the intent of providing effective, safe, convenient, and acceptable products. Barrier contraceptive methods presently in use include condoms, diaphragms, cervical caps, and spermicidal creams, foams, foaming tablets, and melting suppositories. Both the cervical cap and the diaphragm must be fitted by trained medical personnel, and must be refitted/replaced on a regular basis. Condoms may interfere with the sensations of the users, and chemical barrier contraceptives such as jellies, foams, tablets, and suppositories are often messy to use, and frequently cause irritation to the user and/or her partner; all barrier methods currently in use do not allow spontaniety since sexual activity must be interrupted.

A numer of factors influence the effectiveness of barrier contraceptives, including failure of the user to use the method correctly and consistently. A further problem influencing the effectiveness of the spermicidal foaming tablets and suppositories is the time from the insertion of the product into the vagina to the time the suppository has melted or foamed. This time varies among the different chemical barrier products. There are also considerable variations in the melting or foaming times among women using the same product. Moreover, while the effectiveness of melting or foaming suppositories is necessarily dependent on the spermicide incorporated, it will also depend on the chemical content of the base material and the dispersion of the product in the vagina.

SUMMARY OF THE INVENTION

The present invention is directed to a vaginal device adapted for insertion and placement in the human vaginal cavity and subsequent removal therefrom for the local administration of a spermicide or a variety of medicaments.

The device is a sponge-like structure which has a spermicide or medicament contained therein. The present invention enables a sponge-like structure to be formed which is flexible and which can be molded into a wide range of various shapes and sizes but which permits retention of spermicide or medicament therein for great lengths of time. A device product in accordance with the present invention may be used in the vagina for a period up to several days, and will still be biologically active in terms of gradual release of spermicide or other medicament thus improving the device's effectiveness as a drug delivery means.

The device is a polymeric sponge tampon containing a spermicide and/or other medicament. The spermicide also acts as a surfactant/foaming agent to the prepolymer during the polymerization of the sponge. This vaginal device provides a number of advantages in use, some of which are enumerated as follows:

(1) The sponge is a simple contraceptive or medicament-dispensing device which can be inserted in privacy without a special applicator. When the device is used only to deliver spermicide, no prescription is necessary.

(2) The sponge carrier is biocompatible, nontoxic, and nonirritating. When the device is impregnated with spermicide, there are no adverse side effects from its use. The foaming agents and jells/creams used in other spermicidal products, which often cause irritation, are not required with the sponge device.

(3) When in place, the sponge is soft and is not felt by the user; when used as a contraceptive, the device is so natural and soft in feeling that typically neither sexual partner is aware of its presence.

(4) The dimple indentation on one side of the sponge not only allows the sponge to naturally orient itself over the cervix increasing the blocking action of the device, but it also permits deeper placement in the vagina decreasing the chance of interference during coitus; further, the dimple allows the sponge to fold, making insertion and removal easier.

(5) When used to deliver spermicide, the device is reusable with long lasting spermicidal activity. During the recommended two-day wearing period, intercourse can occur multiple times without the need to add any spermicide as long as the sponge remains in the vagina. This reusability makes its cost compare favorably with other barrier contraceptives.

(6) The device is an effective vaginal contraceptive alone, which need not be used in conjunction with creams, jellies, or suppositories of any type. This effectiveness is achieved by a combination of three methods of contraceptive action:

(a) It mechanically blocks the cervical opening when inserted.

(b) It absorbs ejaculate (semen and sperm), thereby decreasing the number of sperm available for fertilization.

(c) It chemically immobilizes sperm by slowly releasing a spermicide.

As a medicament-delivering device, the device has several advantages over the prior art devices:

(1) It is easily inserted and comfortable to use.

(2) Its positioning at the top of the vaginal canal ensures that the medication will be carried down through the vagina as medicament is released from the device.

(3) Because it is placed at the top of the vaginal canal against the cervical opening, it can serve to deliver medicament to the cervix.

(4) It expands the vaginal folds thereby increasing the tissue surface area available to the medicament.

(5) Because of the absorbency of the sponge, vaginal exudate or fluid resulting from the infection being treated is decreased.

(6) The gradual release of the medicament allows a more consistent delivery over time thereby insuring more efficient treatment (and in some cases, use of lesser amounts of medicament) and/or more effective prophylaxis of vaginal infections.

The sponge is formed by mixing a polyurethane prepolymer with an aqueous solution of the spermicide/surfactant; when the sponge is to be used to deliver medication, a specific medicament is also included and the surfactant need not necessarily be a spermicide. After mixing, the blend is poured into a polymeric cavity mold where it begins to foam as hydroxyl groups from the water react with the isocyanate group to form polyurethane. The spermicide in the mixture serves the critical function of a foaming agent which decreases the pore size and increases the softness or resilience of the resulting polymer foam. Without the presence of the surfactant, the physical characteristics of the sponge would drastically differ, probably the most important difference being that the sponge itself would be stiff and abrasive.

BRIEF DESCRIPTION OF THE DRAWINGS

FIG. 5 is a graph comparing the contraceptive efficacy of the vaginal device vs. a foaming contraceptive tablet.

DETAILED DESCRIPTION OF THE DRAWINGS

Figure 1:
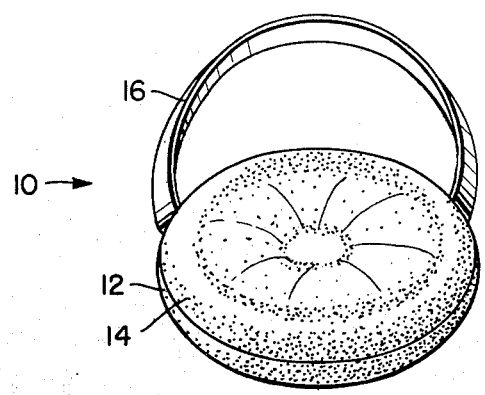
FIG. 1 is a perspective view of the vaginal device.

Referring to the drawings, FIG. 1 illustrates the vaginal device of the present invention 10. A polymeric sponge structure 12 is shown with tiny pores 14 which are in communication with the sponge's environment and which also extend throughout the sponge's innerstructure (not shown). A flexible loop, 16, is molded into the structure 12 to provide a convenient removal means.

Polymeric sponge structure 12 is a soft, pliable porous sponge in the shape of a flattened ball, incorporating a dimple on one side, with a diameter of approximately two inches. Generally, the foam structure is prepared by using polyurethane prepolymer reacted with large amounts of water. The preferred prepolymer is an isocyanate capped polyoxyethylene glycol. A comprehensive description of this prepolymer polyol is given in U.S. Pat. No. 3,903,232, issued to Wood et al, which is hereby incorporated by reference.

The polyoxyethylene polyol used as a reactant in preparing the capped product to be foamed into the sponge of the present invention may have a weight average molecular weight of about 200 to 1,500, with a hydroxyl functionality of 2.2 or greater. The polyoxyethylene polyol is terminated or capped by reaction with a polyisocyanate. This reaction may be carried out in an inert moisture-free atmosphere, such as under a nitrogen blanket at atmospheric pressure at a temperature ranging from about 0° C., to about 120° C. for a period of about twenty hours depending on the temperature and degree of agitation. The polyisocyanates used for capping the polyoxyethylene polyol include the various polyisocyanates set forth in the Wood et al, disclosure.

Capping of the polyoxyethylene polyol may be effected using nearly stoichiometric amounts of reactants. Desirously, however, an excess of isocyanate is used to ensure complete capping of the polyol. Thus, the ratio of isocyanate groups to the hydroxyl groups used for capping is between about 1 to about 4 isocyanate to hydroxyl molar ratio.

To effect foaming and preparation of the sponge structure, a solution of water containing various additives including the spermicide-surfactant and optional medicaments (which need only be dispersed in the water, not completely dissolved therein) is mixed with the urethane prepolymer. The ratio of prepolymer to water is in the range of 30-150 parts by weight prepolymer to 100 parts by weight water. Conversely, the ratio of water to prepolymer is 66-133 parts by weight water to 100 parts by weight prepolymer. If either an excess or a deficiency of water is preset, an incomplete reaction results. In the preferred embodiment, 77.77 parts of the prepolymer are mixed with 100 parts water plus 33.33 parts spermicide/surfactant in order that the volume ratios would result with two volumes of aqueous solution (water plus spermicide) to one volume of prepolymer. This 2:1 volume ratio, which is merely by way of example, was chosen for convenience in order that in the manufacturing process two volume units of water/spermicide mixture could be added to one volume unit of prepolymer.

The final optimum ratios in parts by weight are: 4.5 parts water, 1.5 parts spermicide, and 3.5 parts urethane prepolymer. Any desired medication may be added to the water; the amount of medication added is that sufficient to supply an effective amount of medication over a maximum 48-hour period. This gives the above-indicated volume ratio of 2:1 for the aqueous solution to prepolymer. The aqueous solution contains the spermicide/surfactant, plus any additional medicaments desired.

One of the unexpected and surprising discoveries embodied in this invention is the synergistic combination of a spermicide which also acts as a surfactant with the polyurethane prepolymer. One such spermicide/surfactant is nonylphenoxypolyethoxyethanol herein referred to a Nonoxynol-9, which is a spermicide commonly used in vaginal contraceptive foams, gels, and creams. Other examples of such spermicide surfactants which should be equivalent are p-methanyl phenylpolyoxyethylene ether, polyoxyethylene oxypropylene stearate, polyoxyethylene laurate, glycerol ricinolate, di-isobutyl phenylpoly-oxyethylene ether, tri-isopropyl phenylpolyoxyethylene ether, mono-iso-octyl phenyl ether polyethylene glycol, methoxy polyoxyethylene glycol 500 laureate, polyoxyethylene stearylamine, benzalkonium chloride, cetyl trimethylammonium bromide, methyl benzethonium chloride, benzethonium chloride, sodium dodecylsulfate, di-2-ethylhexyl sodium sulfosuccinate, nonylphenol polyethylene sodium sulfate, sodium oleate, zinc phenosulfonate, dodecylbenzene sulfonate, dodecyl diaminoethyl glycine, and the like.

The acceptable percentage of spermicide in the sponge is greater than 10% and less than 50% dry weight of the sponge, preferably 20%-40% and optimally 30%. The high percentages of spermicide/surfactant present in the claimed invention are unusual because heretofore it was well known that in producing polymer foams it is desirable to use as little surfactant as possible in order to maintain the purity of the resulting polymeric foam. However it was found that the use of these surfactants in percentages of 10% or less produced foams which did not retain the spermicide for any appreciable period. The spermicides were quickly washed out of the sponge, a disadvantage when the user rinses the sponge after one use and expects to reuse the sponge. It was discovered that the surfactant/spermicide concentration must be increased in order to decrease the polymeric cellular foam size and provide a reserve of spermicide, thereby increasing the sponge's capacity to retain the spermicide. In fact, the greater the percentage of surfactant/spermicide used, results directly in a decrease in the cellular pore size of the sponge.

To illustrate the increasing ability of the sponge to retain spermicide after repeated washings as percentage of the spermicide is increased, a series of sponges in the 10%, 20%, and 30% by dry weight Nonoxynol-9 were manufactured and sequentially rinsed. The results of this test series are given in Table A.

Note: This table also includes the effect of pH-reducing additives and presents the effects of these and the Nonoxynol-9 on the pH of rinses from the sponge. This is discussed subsequently in more detail.

TABLE A

| Sponge Code No. | COMPOSITION | | | | | | pH of Eluate Rinse Number | | | | | | | | Rinse Where Spermicidal Effectiveness Is Lost | | | | |
|---|---|---|---|---|---|---|---|---|---|---|---|---|---|---|---|---|---|---|---|
| | Urethane Only | 10% Nonox | 20% Nonox | 30% Nonox | Preservatives | Citric Acid | 1 | 3 | 5 | 8 | 10 | 15 | 20 | 30 | 40 | 0 | 3 | 5 | 10 | 20 |
| 1 | • | | | | | | 6.6 | 6.6 | 6.4 | 6.4 | 6.2 | 6.2 | 6.2 | 5.9 | 5.8 | • | | | | |
| 2 | | • | | | | | 7.9 | 7.0 | 6.4 | 6.5 | 6.4 | 6.1 | 6.2 | 6.1 | 5.9 | | | | | • |
| 3 | | | • | | | | 4.7 | 4.6 | 4.6 | 4.5 | 4.5 | 4.6 | 5.0 | 5.2 | 5.4 | • | | | | |
| 4 | | | | • | • | | 7.0 | 6.6 | 6.6 | 6.2 | 6.2 | 6.1 | 6.2 | 5.9 | 5.8 | | | | | • |
| 5 | | | | • | • | • | 3.4 | 3.2 | 3.3 | 3.5 | 3.6 | 3.6 | 3.9 | 4.2 | 5.2 | • | | | | |
| 6 | | | • | | • | • | 4.7 | 4.8 | 4.8 | 5.4 | 5.4 | 5.5 | 5.6 | 5.7 | 5.8 | | | | | • |
| 7 | | | | | | • | 3.5 | 3.3 | 3.2 | 3.2 | 3.3 | 3.6 | 3.6 | 4.1 | 4.7 | • | | | | |
| 8 | • | | | | | | 8.4 | 7.8 | 6.7 | 6.4 | 6.2 | 6.1 | 6.2 | 5.9 | 6.0 | | • | | | |

TABLE A-continued

| Sponge Code No. | COMPOSITION | | | | | | pH of Eluate Rinse Number | | | | | | | | | Rinse Where Spermicidal Effectiveness Is Lost | | | | |
|---|---|---|---|---|---|---|---|---|---|---|---|---|---|---|---|---|---|---|---|---|
| | Urethane Only | 10% Nonox | 20% Nonox | 30% Nonox | Preservatives | Citric Acid | 1 | 3 | 5 | 8 | 10 | 15 | 20 | 30 | 40 | 0 | 3 | 5 | 10 | 20 |
| 9 | | | | | o | | 8.0 | 7.0 | 6.8 | 6.8 | 6.2 | 6.0 | 6.0 | 5.8 | 6.2 | | o | | | |

The following conclusions can be drawn from the spermicidal effectiveness test summarized in this table:

(1) At least 30% of Nonoxynol-9 is required if the sponge is likely to be washed and reused.

(2) There appears to be a sharp increase in spermicidal effectiveness and sustained release between 20% Nonoxynol-9 and 30% Nonoxynol-9 (5 rinses vs. 20 rines).

(3) A sponge containing 30% Nonoxynol-9 retains spermicidal effectiveness up to 20 rinses.

(4) Addition of pH reducers (e.g., citric acid) to Nonoxynol-9 do not measurably increase spermicidal action.

In preparing additional sponges, it was found that if the percentage of spermicide is much above 50%, the sponge will become quite viscous (mushy) and sticky, which is an unacceptable condition. However, by increasing the dry weight percentages of spermicide to up to 50%, and preferably around 30%, a reserve of spermicide is available in the sponge and the cellular pore size in the sponge is decreased with a greater capacity to retain the spermicide. This decrease in cellular pore size in the sponge has made it unnecessary to include a spermicide retaining additive such as the collagen fibers disclosed in Ser. No. 810,109 of June 27, 1977. This is quite an important result, since collagen presents several problems of quality control, paticularly with regard to purification.

Several additives may optionally be added to the water solution in addition to the spermicide and (optional) drug. For example, various preservatives, antifungal agents, antibacterial agents, antiviral agents, and antioxidants may be added. Additionally, pH adjusters may be added. In the preferred embodiment, to USP purified water is added 0.1% (by weight) benzoic acid, 0.2% sorbic acid, 0.05% sodium hydroxide, 0.5% citric acid anhydrous, and 0.05% sodium metabisulfite.

The benzoic acid and sorbic acid act as preservatives to prevent bacterial or fungal growth from occurring, especially in cases where the sponge is stored between uses.

The citric acid is used as a preservative and also to lower the pH of the sponge to the pH of the vagina, which is typically approximately 4.0 to 5.0. If the vaginal pH is increased too much above this range, bacteria can begin to grow. For example, the gonococcus bacillus is very fragile, and cannot survive in a low pH environment. Furthermore an acid environment is hostile to sperm, and will eventually decrease the sperm mobility to total incapacitation. The citric acid is buffered by reaction with the sodium hydroxide resulting in sodium dihydrogen citrate. Sodium citrate can also be used as a buffer, but sodium hydroxide is preferable.

The sodium metabisulfite serves as an antioxidant, thereby depressing any oxidation processes which might occur.

This additive solution is given to disclose the preferred embodiment. Acceptable ranges for these additives can be found in the following publications: *Remington Pharmaceutical Sciences*, 15th Edition, 1975, Mack Publishing Company; *Martindale Pharmacopoeia*, Pharmaceutical Press, London; *The United States Pharmacopoeia*, United States Pharmacopoeia Convention, Inc.; *The Merck Index*, Merck & Company, Inc. These additives are purely optional and could be omitted entirely while remaining within the framework of the claimed invention.

Further insight into the effect of these additives (the preservatives and the citric acid) is also obtained from Table A. Table A summarizes pH data for the nine sponges as listed and also illustrates the increasing ability of the sponge to retain spermicide after repeated washing as the percentage of the spermicide is increased.

The additional conclusions that can be drawn from the experimental results depicted in Table A include the following:

1. Increasing percentages of Nonoxynol-9 decreases the pH to more acid levels.

2. The preservatives (primarily benzoic acid and sorbic acid) contribute strongly to acid pH.

3. Citric acid contributes strongly to an acidic pH level and the 2% by dry weight used in this Table A brings the pH to below the range of the normal vagina (pH 4 to 5).

4. The pH effect of citric acid and preservatives is essentially gone by the 20th rinse.

For using the vaginal device of the present invention to deliver medication to the vagina or the cervix, an effective amount of the desired drug is incorporated in the aqueous solution as mentioned previously, which is then mixed with the polyurethane prepolymer. Suitable drugs which can be delivered by the vaginal device of the present invention include, without limitation:

1. Anti-infectives, such as antibiotics, including penicillin, tetracycline, chlortetracycline, bacitracin, nystatin, streptomycin, neomycin, polymyxin (sulfate salt form), gramicidin, oxytetracycline, chloramphenicol, and erythromycin; sulfonamides, including sulfamethizole, and sulfisoxazole; antivirals, including idoxuridine; and other topical antibacterials including nitrofurazone, providone-iodine, and sodium propionate;

2. Anti-inflammatories such as hydrocortisone, cortisone, dexamethasone, fluocinolone acetonide, triamcinolone, and various prednisolone compounds.

3. Estrogenic steroids such as estrone, 17 N-estradiol, ethinyl estradiol, and diethylstilbesterol; and 4. Progestational agents such as progesterone, 19-norprogesterone, norethindrone, megestrol, ethisterone, medroxy progesterone, norethynodrel, and 17-hydroxy-progesterone;

5. Prostaglandins such as $PGE_1$, $PGE_2$, $PGF_1$, $PGF_{2\alpha}$ and the like.

The drugs can be in a variety of forms, such as uncharged molecules, components of molecular complexes, or nonirritating, pharmacologically acceptable salts such as hydrochloride, hydrobromide, sulfate, phosphate, nitrate, borate, acetate, maleate, tartrate, salicylate, and the like. For acidic drugs, nontoxic salts of metals, amines, or organic cations (e.g., quaternary ammonium) can be used. Additionally, simple derivatives of the drugs such as ethers, esters, amides, and the like which have desirable retention and release characteristics but which are easily hydrolyzed by body pH, enzymes, etc., can be used.

The amount of drug incorporated in the vaginal device of the present invention varies, depending on the particular drug, the desired therapeutic or prophylactic effect, and the time span for which the device provides therapy. The upper limit and the lower limit will depend on the activity of the drug and the time span of its release from the device. Thus, it is not practical to define a range for the therapeutically effective amount of drug to be incorporated in or released by the vaginal device.

In connection with the present invention, "drug", "medication", or "medicament" broadly includes without limitation physiologically or pharmacologically active substances for producing localized systemic effect or effects in animals especially mammals.

The above drugs and other drugs can be present in the vaginal device alone or in combination with pharmaceutical carriers to make the drugs more easily dispersible in the prepolymer mixture. The carrier may also contain adjuvants for preserving, stabilizing, wetting, emulsifying, and the like.

Figure 2:
FIG. 2 is a cross-sectional view of a two-cavity mold.

An important aspect of the claimed invention is the method of manufacture of the end product polymer sponge and its packing. It is critical in this type of product that the product be produced under sanitary (not necessarily sterile) conditions. This is often difficult where a product has to be handled after its manufacture. The packaging and sanitation problem has been solved by incorporating the spermicide and/or medicaments during manufacture and molding the sponge in a polymer mold which can serve as the final product package. Referring to FIG. 2, the mold is shown as an upper half 18 and a lower half 20. The material and surface finish of the mold are important in several respects.

First, the surface of the mold is critical in forming the exterior characteristics of the sponge. For example, in forming the sponge upon foaming, there is a tendency for the sponge to form a shiny skinlike, closed-cell, surface of its exterior. This is quite undesirable, as the sponge will not absorb sperm as well, nor will it release spermicide or other medication as well. It has now been discovered that polypropylene or polyallomer are acceptable polymers to use for the mold; the polyallomer is manufactured by Eastman Chemical Products, Inc., Plastics Division, Kingport, Tenn. These two polymers have been found to be especially advantageous, particularly, as they are currently used for intravenous solution bottles. Both polypropylene and the polyallomer have been found to be successful in preventing any skin formation in the contraceptive sponge.

Secondly, and probably more important than the actual material of the mold, the surface finish of the mold must not be smooth. A smooth mold surface finish will produce a sponge with a shiny skin. However, a finish of about 60 grit, or a finish resulting from the use of fine deep etch on the injection mold used to make the sponge molds, provides a rough finish which will prevent any skin formation.

Figure 3:
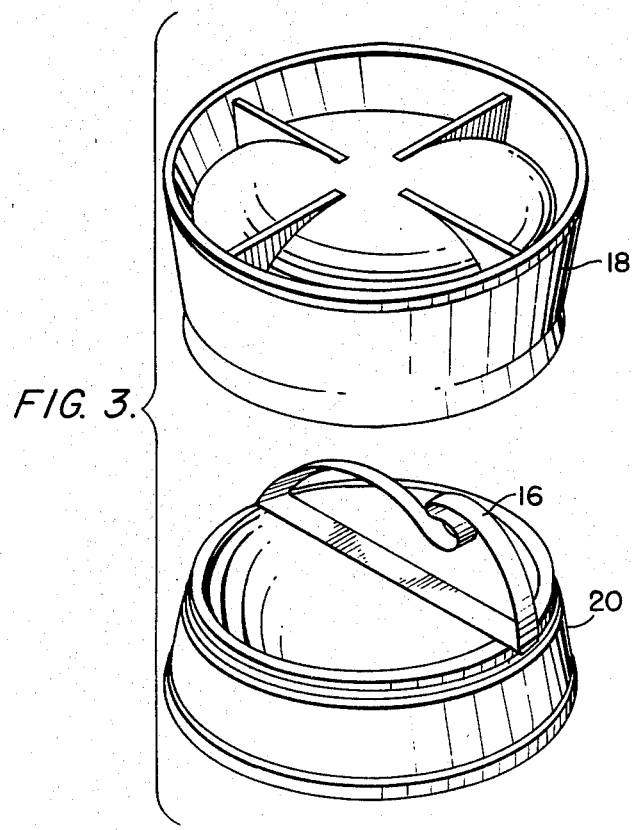
FIG. 3 is a perspective view illustrating the placement of the loop and closing of the mold.

Continuing with the manufacturing procedures description, two volumes of the water/spermicide solution are mixed with one volume of the urethane prepolymer in preparing the preferred embodiment of the sponge. Mixing is effected by a high shear mixer which produces a creaming action, after which the mixture is poured or ejected into the mold halves to begin foaming and cure. The foam forms by spontaneous exothermic reaction, filling the two mold halves. Just before the mold halves are closed, a soft Dacron ® polyester ribbon loop 16 as shown in FIG. 3 is laid over one half of the mold 18, and the other half is quickly closed over half 18 with the loop inbetween.

Figure 4:
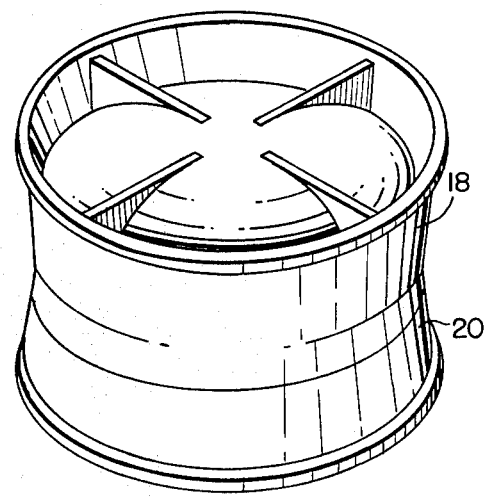
FIG. 4 is a perspective view of the vaginal device as packaged.

With the mold closed, the polymer continues to foam with the air and carbon dioxide reaction product escaping out through the mold seam so that no air bubbles are trapped in the sponge. The shot size of material poured into the mold is measured precisely so that the sponge will just fill the container. While the air and carbon dioxide escape through the mold seam as the foam blows, the polymer mixture is retained since it is more viscous than the air and is nearly fully cross-linked. Shortly after the foaming operation is completed (about 5 minutes later) the mold is opened, the sponge automatically removed and inspected, and packaging of the final sponge product carried out under clean conditions. The product is then ready to be sold commercially, as shown in FIG. 4. As mentioned above, it is also possible to use the mold as the final package and the product is in that case never removed from the mold; this further reduces the opportunity for contamination of the product to occur.

The loop 16 on the sponge allows the vaginal device to be easily grasped for removal from the vaginal canal. The removal loop is made from 100% woven or briaded polyester, which is soft, nonirritating, and biocompatible. As stated previously, the dimple in the sponge allows it to fold, thus making insertion and removal easier.

The in-vivo release of Nonoxynol-9 from the vaginal device of the present invention (without coitus) is shown in Table B. The sponges used all contained approximately 30% Nonoxynol-9. The sponges were worn by women volunteers for the time periods shown and the corresponding amounts of spermicide released are given. The sample of women involved at each time period was small, the standard deviations were large, and the variation among women was substantial; statistical confidence requires a larger sample.

TABLE B

| IN-VIVO RELEASE OF SPERMICIDE FROM SPONGE | |
|---|---|
| Length of Time Sponge Worn | Nonoxynol-9 Delivered |
| 0 (insert & remove) | 80 |
| 1 Hour | 150 |
| 4 Hours | 160 |
| 12 Hours | 100 |
| 1 Day | 140 |
| 2 Days | 240 |

The vaginal device comprising Nonoxynol-9 was tested post-coitally for effectiveness. Eleven women participated in the study with each data point recorded at mid-cycle in subsequent months, for a total of four months for each woman. Both placebo (non-medicated) and active (30% Nonoxynol-9) devices were tested in women with a history of fertility. Delfen ® contraceptive foam (Ortho Pharmaceuticals Corp.) was used for comparison. Baseline data reflect normal, non-contracepting values for post-coital testing (PCT). The results of these studies are shown in Table C.

The numbers represent mean quantitative measures of vital sperm per field. A value of less than four (4.0) is considered infertility. It should be noted that the placebo device has some effect, indicating that the blocking/absorbing actions of the device do have a role in its effectiveness. The last column represents a one-hour retest for the active device.

The vaginal device of the present invention containing 30% Nonoxynol-9 (trademarked COLLATEX and, more recently SECURE) was compared in human use-effectiveness to Neo-Sampoon ® foaming contraceptive tablets (Eisai Co. Ltd., Tokoyo). The results of this study can be seen in FIG. 5. The sponge device had a pregnancy rate less than the foaming tablet (greater effectiveness) and a lower discontinuation rate as well (greater acceptability to the user). These trials were subsequently extended to a broader base of users as described in the next paragraph.

TABLE C
POST-COITAL TEST DATA SUMMARY

| Subject Code | Baseline | Medicated Sponge | Non-medicated Sponge | Delfen Foam | Medicated Sponge Sequence Hour |
|---|---|---|---|---|---|
| 01 | 45.66 | 0.53 | 76.40 | 0 | 0.60 |
| 02 | 7.16 | 0.60 | 21.70 | 0 | n.a. |
| 03 | 17.61 | 0 | 29.80 | 0 | 0 |
| 04 | 7.20 | 3.80 | 0 | 0 | 3.09 |
| 05 | 28.90 | 2.50 | 33.50 | 0 | n.a. |
| 06 | 19.70 | 4.03 | 4.60 | 0 | 0.99 |
| 07 | 0.39 | 1.50 | n.a. | 3.20 | 0 |
| 08 | 48.86 | 0.70 | 2.20 | 0 | n.a. |
| 09 | 69.50 | 0.07 | 0.53 | 0 | n.a. |
| 10 | 7.93 | 0 | 2.93 | 0 | 0 |
| 11 | 11.40 | n.a. | 17.06 | 0.26 | n.a. |

The vaginal device of the present invention was tested clinically in comparison with several other vaginal barrier contraceptives. These clinical trials involved approximately 800 women using the sponge for a total of more than 8,000 woman-months of use. Pregnancy rates on the Life Table analysis basis are approximately 6 per 100 woman-years. The incidence of discontinuation for disconfort was about 1.5%, and for medical reasons (e.g. allergic response) was about 0.5%. There were no complications or adverse reactions associated with the use of this vaginal device in these world-wide clinical trials. The effectiveness level experienced is approximately that achieved with the intrauterine device and exceeds other barrier methods in effectiveness as a contraceptive.

While the above clinical trials for contraceptive effectiveness used the "dimpled" configuration of the vaginal device discussed previously, when the vaginal device is to be used as a drug-delivery device, it may be in any form that is comfortable to the wearer, i.e., sphere, cylinder, prolate spheroid (football), or the like. As the drug-delivery device does not need to be designed not to interfere with intercourse, or to cover the cervix, the device can be in any configuration that will be contained in the vagina and is comfortable to the wearer.

Because of a natural concern for biological stability of the device, as well as the more recent awareness of the so-called "Toxic Shock Syndrone" associated with menstrual tampons, the effect of the preservatives contained in the vaginal sponge device of the present invention, incorporating 30% Nonoxynol-9, on a series of standard microbes as well as on the vaginal microbial environment was studied. A series of in vitro tests using devices fresh from their packages as well as sponges clinically worn for two days were subjected to microbiological evaluation. The vaginal devices were inoculated with each of the following test organisms: E. coli, Staph. aureus, Candida albicans, Pseudomonas aeruginosa, and Aspergillus niger (all from American Type Culture Collection), and "Toxic Shock Syndrome" Staph. aureus (Harrisburg Strain). The protocol followed was of USP XX Microbiological Tests "5", modified to account for the sponge material. The sponge device did not support the growth of any of the test organisms, nor did it significantly alter the vaginal environment after two days use. These tests support the role of the preservatives and the effectiveness of the sponge carrier/delivery system for these compounds.

DETAILED DESCRIPTION OF THE INVENTION

The following examples are set forth in order to clearly point out the detailed description of the invention, but are not intended to limit the invention. Throughout the specification and the following examples, all parts are expressed in parts by weight unless otherwise indicated.

EXAMPLE 1

8 parts urethane prepolymer were mixed with a solution consisting of 2 parts Nonoxynol-9 surfactant/spermicide and 8 parts of water. This produced a sponge with fine cell structure and a Nonoxynol dry weight content of 20%.

EXAMPLE 2

18 parts of the urethane prepolymer were mixed with a solution consisting of 2 parts Nonoxynol-9 surfactant/spermicide and 16 parts water. This produced a sponge which had a Nonoxynol dry weight content of 10% and have a sponge which was soft and flexible but that did not retain the spermicide to a fully acceptable degree.

EXAMPLE 3

8 parts of the urethane prepolymer were mixed with a solution consisting of 2 parts Nonoxynol-9 surfactant/spermicide and 5 parts water. This gave a 20% by dry weight spermicide sponge with a fine cell structure of a lower weight and more resilience than a sponge produced from equal weights of water and polymer.

EXAMPLE 4

The urethane prepolymer in Example 3 was heated to about 110° F.; there was more foaming of the polymer and a sponge resulted which had slightly larger cells and lower cellular density than the sponge in Example 3.

EXAMPLE 5

16 parts of the urethane prepolymer were added to a solution consisting of 4 parts of Nonoxynol-9 surfactant/spermicide and 14 parts water and 0.1% USP benzoic acid as a preservative. This produced a 20% spermicide sponge of good quality which was clinically acceptable.

EXAMPLE 6

16 parts of the urethane prepolymer were added to a solution consisting of 4 parts Nonoxynol-9 surfactant/spermicide and 12 parts water and 1/10 of 1% benzoic acid added to the water. The resulting sponge contained 20% spermicide and was of somewhat lesser weight than the sponge of the previous example and had slightly finer cell size.

EXAMPLE 7

16 parts of the urethane prepolymer were added to a solution consisting of 4 parts of Nonoxynol-9 surfactant/spermicide and 12 parts water and 0.16 parts zinc sulphate. This gave a 20% spermicide sponge of good quality which was clinically acceptable, although the zinc sulfate caused slightly larger cell size.

EXAMPLE 8

14 parts of the urethane prepolymer were added to a solution consisting of 6 parts of Nonoxynol-9 surfactant/spermicide, 12 parts water and 0.16 parts zinc sulphate. These 30% spermicide sponges were acceptable although the cell size was somewhat larger because of the zinc sulphate.

EXAMPLE 9

16 parts of urethane prepolymer are added to a solution consisting of 4 parts of Nonoxynol-9 surfactant/spermicide plus 5 mg. PGE, 14 parts water, and 0.1% USP benzoic acid as a preservative.

EXAMPLE 10

16 parts of urethane prepolymer are added to a solution consisting of 4 parts Nonoxynol-9 surfactant/spermicide plus 25 mg. progesterone, and 12 parts water.

EXAMPLE 11

16 parts of urethane prepolymer are added to a solution consisting of 6 parts Nonoxynol-9 surfactant/spermicide, 12 parts water, and 0.3 parts of nystatin.

EXAMPLE 12

16 parts of urethane prepolymer are added to a solution consisting of 4 parts Nonoxynol-9 surfactant/spermicide, 12 parts water, and 1 part providone-iodine.

What is claimed is:

1. A vaginal device adapted for insertion and placement in the human vaginal cavity and subsequent removal therefrom, comprising:
    a spermicide-foaming agent in a dry weight percentage of from about 10% to about 50%, and
    a water-catalyzed foamed urethane polymer from which the spermicide is slowly released from the sponge during use.

2. The vaginal device of claim 1 including a drug for local delivery to the vaginal area, which drug is slowly released from the device during use.

3. The vaginal device of claim 1 including a non-toxic acid for lowering the pH of the device to between 4.0 and 5.0.

4. The vaginal device of claim 1 wherein the dry weight percentage of spermicide-foaming agent is at least 30%.

5. The vaginal device of claim 1 wherein the spermicide-foaming agent is nonylphenoxy polyethoxyethanol.

6. The vaginal device of claim 1 wherein the urethane polymer is water catalyzed from an isocyanate-capped hydrophilic polyoxyethylene polyol.

7. The vaginal device of claim 1 being in the shape of a flattened ball, one side of the device having a recess contoured to fit over the os of the cervix.

8. The vaginal device of claim 1 wherein the dry weight percentage of the spermicide-foaming agent is at least 30%.

9. A vaginal device adapted for insertion and placement in the human female vaginal cavity and subsequent removal therefrom, for the local administration of a drug, comprising:
    a drug for local delivery to the vaginal area,
    a foaming agent in a dry weight percentage of form about 10% to about 50%, and
    a water-catalyzed foamed urethane polymer from which the drug is slowly released from the sponge during use.

10. The vaginal device of claim 9 wherein the drug is selected from the group consisting of anti-infectives, anti-inflammatories, estrogenic steroids, progestational agents, and prostaglandins.

11. The vaginal device of claim 9 being in the shape of a flattened ball, one side of the device having a recess contoured to fit over the os of the cervix.

12. A method for forming a vaginal device adapted for insertion and placement in the human vaginal cavity and subsequent removal therefrom; and
    mixing from about 10% to 50% by dry weight of a foaming agent with a water-catalyzed, foam-forming urethane prepolymer and a dry agent for local delivery to the vaginal area; and
    permitting the mixture of prepolymer, compound, and foaming agent to foam and form a stable, flexible, sponge-like structure from which the drug is slowly released from the sponge-like structure while in the vagina over a period of time.

13. The vaginal device of claim 12 being in the shape of a flattened ball, one side of the device having a recess contoured to fit over the os of the cervix.

14. The method of claim 12 wherein the foaming agent is a spermicide.

15. The method of claim 12 wherein the drug is selected from the group consisting of anti-infectives, anti-inflammatories, estrogenic steroids, progestational agents, and prostaglandins.

16. The method of claim 12 wherein the urethane prepolymer is an isocyanate-capped hydrophilic polyoxyethylene polyol.

17. A method for forming a vaginal device adapted for insertion and placement in the human vaginal cavity and subsequent removal therefrom, the device for the local administration of a spermicide, comprising:
    mixing from about 10% to about 50% by dry weight of a spermicide-foaming agent with a water catalyzed, foam-forming urethane prepolymer; and
    permitting the mixture of prepolymer and spermicide-foaming agent to foam and form a stable, flexible, sponge-like structure from which the spermicide-foaming agent is slowly released from the sponge structure while in the vagina over a period of time.

18. The method of claim 17 wherein the prepolymer is an isocyanate-capped hydrophilic polyoxyethylene polyol.

19. The method of claim 17 wherein the spermicide-foaming agent is nonylphenoxypoly ethoxyethanol.

20. The method of claim 17 wherein the dry weight percentage of spermicide-foaming agent is at least 30%.

21. The method of claim 17 wherein a drug intended for local delivery to the vaginal area is mixed with the spermicide-foaming agent and the prepolymer.

22. The method of claim 17 wherein a non-toxic acid is mixed with the spermicide-foaming agent and the prepolymer in quantity sufficient to lower the pH of the device to between about 4.0 and 5.5.

23. The method of claim 17 wherein the vaginal device is generally in the shape of a flattened ball, one side of the device having a recess contoured to fit over the os of the cervix.

24. A method of delivering an effective amount of a drug to the vaginal area comprising inserting into the human female vagina the device of claim 2.

* * * * *